(12) United States Patent
Piety (10) Patent No.: US 9,406,097 B1
(45) Date of Patent: Aug. 2, 2016

(54) HEALTH CARE INFORMATION SYSTEM

(75) Inventor: Kenneth R. Piety, Knoxville, TN (US)

(73) Assignee: Transition Innovation, LLC, Knoxville, TN (US)

( * ) Notice: Subject to any disclaimer, the term of this patent is extended or adjusted under 35 U.S.C. 154(b) by 2099 days.

(21) Appl. No.: 11/333,420

(22) Filed: Jan. 17, 2006

(51) Int. Cl.
G06Q 10/00 (2012.01)
G06Q 50/24 (2012.01)

(52) U.S. Cl.
CPC ................................ *G06Q 50/24* (2013.01)

(58) Field of Classification Search
CPC .............................. G06F 19/322; G06Q 10/10
USPC ............................................................ 705/3
See application file for complete search history.

(56) References Cited

U.S. PATENT DOCUMENTS

| | | | | |
|---|---|---|---|---|
| 5,644,778 | A * | 7/1997 | Burks et al. | 705/2 |
| 5,832,450 | A * | 11/1998 | Myers et al. | 705/3 |
| 6,463,417 | B1 | 10/2002 | Schoenberg | |
| 6,523,009 | B1 | 2/2003 | Wilkins | |
| 2002/0026332 | A1* | 2/2002 | Snowden et al. | 705/3 |
| 2002/0029157 | A1 | 3/2002 | Marchosky | |
| 2002/0091548 | A1 | 7/2002 | Auer et al. | |
| 2002/0120472 | A1 | 8/2002 | Dvorak et al. | |
| 2002/0123909 | A1 | 9/2002 | Salisbury | |
| 2002/0138306 | A1 | 9/2002 | Sabovich | |
| 2002/0194027 | A1* | 12/2002 | Smith | 705/2 |
| 2003/0050803 | A1* | 3/2003 | Marchosky | 705/3 |
| 2003/0088440 | A1 | 5/2003 | Dunn | |
| 2003/0088441 | A1 | 5/2003 | McNerney | |
| 2003/0115084 | A1 | 6/2003 | Gage | |
| 2003/0158754 | A1 | 8/2003 | Elkind | |
| 2003/0208381 | A1 | 11/2003 | Walter | |
| 2004/0030586 | A1 | 2/2004 | Cucchiara | |
| 2004/0078240 | A1 | 4/2004 | Katz | |
| 2004/0111298 | A1 | 6/2004 | Schoenberg | |
| 2004/0117215 | A1 | 6/2004 | Marchosky | |
| 2004/0172307 | A1 | 9/2004 | Gruber | |

(Continued)

FOREIGN PATENT DOCUMENTS

WO    WO 03085577    10/2003

OTHER PUBLICATIONS

CapMed, "Personal Health Record (PHR) User's Manual", Copyright 1996-2004, pp. 1-124.
Markle Foundation, The Robert Wood Johnson Foundation, "Linking Health Care Information: Proposed Methods for Improving Care and Protecting Privacy", Feb. 2005, pp. 1-73.

(Continued)

*Primary Examiner* — Hiep V Nguyen
(74) *Attorney, Agent, or Firm* — Luedeka Neely Group, P.C.

(57) ABSTRACT

In a method for creating and managing personal medical records a request for health care information is sent to a third-party payer, and health care information is received from the third-party payer and used to create received health care information. A patient profile identifies the types of health care information the patient wishes to obtain and save, and the received health care information is processed based on the patient profile to produce a result that includes one or more of (a) health care information that the patient wishes to save and was directly obtained from the received health care information, (b) the identity of health care information that was suggested to exist by the received health care information and that the patient wishes to save, but that was not contained within the received health care information. Based on the result, a web based computer or a patient's computer creates and manages personal medical records. The computer may create and transmit a request for additional health care information that was suggested to exist.

8 Claims, 2 Drawing Sheets

(56) References Cited

U.S. PATENT DOCUMENTS

| | | |
|---|---|---|
| 2004/0243441 A1 | 12/2004 | Bocionek et al. |
| 2005/0010446 A1* | 1/2005 | Lash et al. .................. 705/2 |
| 2005/0010452 A1 | 1/2005 | Lusen |
| 2005/0021376 A1 | 1/2005 | Zaleski et al. |
| 2005/0027568 A1 | 2/2005 | Dorris |

OTHER PUBLICATIONS

American Health Information Association, "AHIMA Workgroup on Core Data Sets as Standards for the EHR", E-HIM Strategic Initiative: Core Data Sets (AHIMA Practice Brief). Journal of AHIMA 75, No. 8 (Sep. 2004): 68A-D.

Onfile Advertisement.

* cited by examiner

HEALTH CARE INFORMATION SYSTEM

FIELD

The present invention relates to the field of creating and maintaining patient health care and fitness records, particularly, electronic health care records.

BACKGROUND

One goal of this health care information system is to empower the individual to be responsible for his own health care or for the health care information of those for whom he is the primary caregiver by providing access to important health-related information. An individual is the primary health care manager for himself and, in some cases, for his dependents. No one has more vested interests in having access to complete and accurate personal health records than the individual. The present system gains importance as we attempt to care for children, elderly parents, relatives or friends and other groups of people, especially those with chronic health problems. Also, the system is useful even to those with relatively few current health issues, in part, bedause it ensures that needed health information will be available to support future concerns that will certainly develop.

Presently, almost no one has a complete record of their personal health information. Most health care providers maintain only the information related to their services for a limited period of time and then such records are destroyed. There are some software programs available which allow the individual to manually compile information related to the health services that he or she has received. These programs also allow other information to be entered which the individual may want to track. These systems are targeted directly at benefiting the individual but are very labor-intensive.

In accordance with the present invention, a system is provided that targets the individual and provides at least summary information from health care providers automatically. Although many health care providers do not maintain electronic records, the summary information necessary to request payment from third-party payers, such as insurance companies, are all currently done electronically in a standardized format as specified by the HIPPA ASC X12 Implementation Guide. Health insurance companies and other third-party payers maintain all of their records in an electronic form, typically, and thus represent a very convenient place to obtain the summary of all services for which any health provider requests payment, and the actual amounts paid by insurance and due from the individual. This information is compiled by the present system for the individual and for those under his or her care.

The information transmitted to the third-party payer is combined and integrated with the information provided by the patient and the health care provider. Thus, the present system provides a very powerful tool for managing health care for an individual and his or her dependants. Using this system, insurance companies transmit the health information which they received for an individual to a secure web sites given proper authorization. It requires minimal effort for an insurance company to forward the information because the insurance company sends and receives the information in a standardized electronic format.

In addition, the insurance company may send explanations of benefits, preferably electronically, which confirms the information provided by the requests-for-payment. The system optionally may make use of the explanation of benefits as a double check on the information obtained from the requests-for-payment. The present system augments and is in concert with the intent of HIPPA which clearly states that an individual's medical records belong to the individual. Electronic versions of these health records are forthcoming and will create greater efficiencies in the present system and in the health care system as a whole. The information sent to health insurance companies (or other third-party payers) along with the data that an individual collects for himself allows an individual to make better health care decisions for himself, his loved ones and others. We recognize the importance of obtaining and managing our own financial records which only affect our net worth. We incorrectly assume that others are responsible for managing our health information which may eventually affect the quality or duration of our lives.

In one embodiment, the present invention is a distributed system that places the individual in control of his health care information using software on a local computer and using secure transmissions to a website. Such transmissions may be a direct Internet connection to the website or transmissions may occur with the system through e-mail or other types of communication. Using Internet connections, e-mail, faxes, and regular mail, the system automatically obtains information from insurance companies (third-party payers) initially, and using the insurance company information seeks information from actual providers. The arrival of data from the insurance company serves to automatically, at the user's option, generate a request for specific data from the provider. The request may be sent to the provider through an Internet connection or by e-mail, mail or fax transmission. The provider is requested to give the individual part or all of the records associated with the identified services. The faxes or e-mail from the provider may be sent to locations serviced by the website or to the individual. Preferably, the faxes, e-mail or even letters are scanned, as needed, and stored electronically. This system improves efficiency and reduces expense or obtaining records especially where the records are not in digital format.

In accordance with another aspect of the system, it interviews the individual prior to visiting the office of a provider and summarizes important observations and may generate a written report. The report may include a written request for health care information that may be signed and provided to the provider at the time of service. Such request may also request that the requests-for-payment be directed to a specified patient defined place, which may be an email address of the current invention. The computer at the patient defined place will process the requests-for-payment to extract information from the document in the manner described herein and will then forward the requests-for-payment to the appropriate party for payment.

The secure website may also serve as a backup storage location for the complete health history of the individual and may serve as a source of emergency medical information if the individual so elects. The software which creates and maintains the health data repository on the personal computer will index all information so that information is presented or searched logically, preferably chronologically. Synchronization with data transmitted to the secure website is done on a periodic interval and a backup copy of the synchronized health care data repositories can be uploaded to the secure site on a prescribed interval. The individual's personal computer typically includes software that handles security issues to prevent unauthorized access and provides both standard reports and customized searches to locate information. Data for any individual in the data repository may be extracted and/or removed as the individual elects to relocate his health information, such as when a child becomes an adult and chooses to move his information. The system allows any type of data file to be inserted into the repository but unrecognized formats may require additional software to provide presentation and other utilization of that information. An interesting aspect of the system is the ability to retain files that are authenticated as unaltered from an original source and would have legal validity, such as a birth certificate, a living will, or health care power of attorney.

In this system, there may be a need to follow a special procedure during an initial period where all past records of interest are gathered by the system and records from future visits are collected incrementally. This may be important to expedite the process and reduce the costs. Providers typically use an outside service to handle generic requests for records and it may take up to three weeks to obtain the records and the individual is charged a substantial fee for such copies.

In summary, the system provides numerous tools that may be utilized by an individual to conveniently organize and understand health care information. Functions performed by the system include:

1. Stores copies of important records such as shot records, birth certificates, living wills, wills, organ donor authorization, and current pictures.
2. Generates standard health forms for schools, camps, athletic teams, insurance applications, physicians' offices, etc. . . . .
3. Stores permission forms to grant temporary health decision authorization for a child.
4. Stores emergency medical information.
5. Generates a list of current medications with prescription numbers and dates of validity.
6. Tabular and graphical trends in any variable that the user has elected to chart; for example, height, weight, blood pressure, cholesterol levels, etc.
7. Generates chronological lists or cumulative tallies of important events, such as seizures, breathing distress, a diabetic reaction, high fevers, ear infections, etc.
8. Lists all tests or a specific test that has been performed and where the test results are located.
9. Stores observations, data and events that might be associated with illness or injury that the patient is logging prior to visiting a physician; for example, activities, foods, contacts, temperatures, vomiting, diarrhea, other symptoms, and notebook or diary for recording circumstances.
10. Lists dental services.
11. Lists physician visits or therapy services.
12. Stores an eye examination and specifications of corrective lenses.
13. Stores health expenses records for each individual, family or group.
14. Stores a schedule of doctors' appointments or other medically related tasks with notification options.
15. Stores a contact list for current health care providers and insurance companies or other third-party payers.
16. Recommends appropriate health checks to have performed corresponding to a patient's specific profile.
17. Provides alerts to possible health changes shown in the data related to the patient.
18. Provides heart or fitness profiles and recommendations.
19. Provides access to health information on requested topics by using internal or external searches.
20. Enables the creation of a regimen of therapy or recovery activity with schedules and milestones that will notify user if recovery is not in line with guidelines specified by a health provider.

Some advantages provided by this Invention include:

1. Creating a method for efficiently collecting health care data now when most providers do not maintain their medical records electronically. When all providers have electronic records, a patient may be able to work via direct requests to the providers, but this would not allow automated requests of the health records and the automated filtering of the data requested.
2. Minimizes the effort required from the patient to obtain provider information by working through the standardized, electronic system currently in place to request payment for services rendered.
3. Reduces expense to the patient user by requesting minimum data of interest. Providers are required to provide the data but not free. Providers may charge for costs associated with preparing records, copying, or transmitting.
4. The data from providers is maintained in the same repository with information generated by the user in his daily activities. This may be observations of medically related occurrences or measurements from instruments used at home.
5. Anticipating and reporting possible need for future health care actions based on supplied information.

BRIEF DESCRIPTION OF THE DRAWINGS

The present invention may best be understood by reference to embodiments of the invention illustrated in the attached Figures in which.

DETAILED DESCRIPTION

In the preferred embodiment patient health care records are created and maintained based in part on data generated primarily for third party payers. Forms dictate the way doctors provide request-for-payment to insurance companies and other payers. Information about the above forms can be found at www.disa.org. The forms in question are ANSI ASC X12 837 and 835. Form 837 provides the codes for claims and form 835 provides codes for remittance. In accordance with one aspect of the invention, requests-for-payment information is utilized to facilitate the generation and maintenance of personal health care records owned by an individual that can be relied upon by health care professionals, thereby providing needed information to a provider 21-23 and the patient efficiently and quickly. In accordance with another aspect of the invention, other forms of information provided to third party payers are used to generate and maintain patient health records. Such other forms may include pre-authorization requests made by Providers 21-23 seeking authorization to treat a patient in a particular way and may also include information from a pharmacist, such as the identity of drugs provided to a patient.

Figure 1:
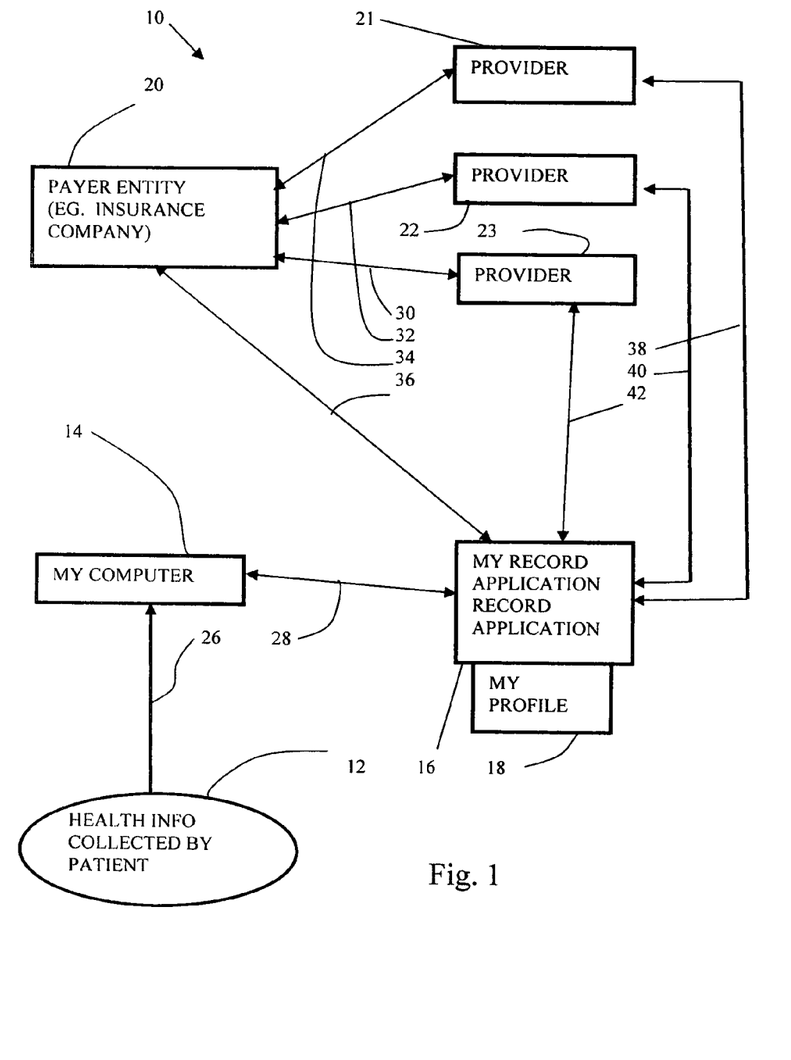
FIG. 1 is a block diagram illustrating a website communicating with a patient's computer, a third party payer entity 20, and health care providers 21, 22 and 23.

In FIG. 1, a block diagram is provided illustrating one embodiment of the invention. Health information 12 is provided by a patient into the patient's computer named My Computer 14. My Computer 14 then to My Record Application 16 and provides my health information 12. In one embodiment, My Record Application 16 is a computer and computer program at a remote location connected by a communication system to My Computer 14, and the communication system in this embodiment in the World Wide Web. In addition, My Computer 14 provides My Record Application 16 with patient identification information, insurance identification information, and health provider information, such as information concerning doctors, hospitals, clinics and the like used by the patient. The patient also sets up a My Profile 18 which tells My Record Application 16 what type of information the patient wishes to obtain and record at the website. The My Profile 18 can also include additional information about the patient or his dependents such as name, age, allergies, etc.

My Record Application 16 takes the information provided by the patient and contacts insurance companies or other payer entities 20. This contact is preferably made electronically to the insurance or other entity, but it could also happen through e-mail, fax, hard copy letter, computer voice, or human voice. My Record Application 16 communicates to the payer entities 20 (insurance companies) a request that the payer entities 20, e.g. the insurance companies, automatically send every request-for-payment to My Record Application 16. Then, the payer entities 20 are expected to provide the request-for-payment information automatically whenever such requests are received. Preferably, the information on the request-for-payment is provided to My Record Application 16 in electronic form. Again, this is preferably a data transfer in which the data is provided in a format that can be understood by the computer at My Record Application 16. However, My Record Application 16 can also receive information by e-mail, fax, hard copy mail, and voice. The user of My Record Application 16 may be prompted to participate in requesting, transferring, scanning, processing and the like as necessary. In an alternate embodiment, the patient may instruct the doctor to send the request-for-payment directly to My Record Application 16, where the request is copied and then sent to the appropriate insurance company or other entity. Or, the doctor may send the directly to the insurance company or other entity, with a copy to My Record Application 16. The requests-for-payment received by My Record Application 16 may be used instead of asking the insurance company to provide them or they may be used as a double check on the insurance company to make sure that all requests-for-payment are being received by My Record Application 16. In such case, My Record Application 16 will check each first to insure that it is not a duplicate of another received earlier.

When My Record Application 16 receives information from an insurance company, it creates an automatic log of the information received. In addition, it interprets the information received. For example, all or most of the information received from the payer company will be in the form of payment codes or request-for-payment codes. The website determines from those codes what services were performed and then records that information in the log in a human readable form. The computer readable information is likewise recorded in the log and can be accessed by the patient, the owner of the website records, upon special request. Normally, a patient would not view the coded information. Instead, the patient would view the interpreted information.

As previously mentioned, the patient also provides My Record Application 16 with a profile called My Profile 18. My Profile 18 is generated through a number of different mechanisms. First, for a very sophisticated user, My Profile 18 may be generated manually. In such case, the user will manually provide the computer with information as to what health records it desires to maintain at the website and what health records are not desired.

A less sophisticated user is offered several options for entering My Profile 18. The checklist option provides the user with a complete list of the information that might be available and it gives the patient the option of obtaining that information or not. For example, the checklist could have a variety of types of health information 12 that might be available. Such information would include things like Chemical Lab Data, blood lab data, heart data, blood pressure, viral checks, X-rays, MRIs, CAT scans, EKGs, and the like. The checklist will also include different types of sicknesses and service Providers 21, 22 and 23 such as a pediatrician, urologist, psychologist, anesthesiologist, etc. Next, since the patient has provided the names of doctors, the checklist may also include the names of specific doctors or other health care Providers 21,22 and 23, such as hospitals, physical therapist, clinics and the like.

Some of the information provided by the checklist might be contradictory. For example, if the patient indicated that he or she did not wish to obtain X-rays, but did wish to obtain everything provided by a particular doctor, a conflict would arise if the particular doctor had an X-ray. The default condition would be to obtain the information in the event of a conflict. However, that default position can be reversed manually by the patient.

My Profile 18 may also be established by a profile wizard. In such case, the profile wizard is actuated and will ask questions about the patient. For example, the wizard will inquire about the history and preferences of the patient. In a preferred embodiment the wizard would inquire as to whether the patient had any history of heart disease or diabetes. The wizard may also inquire about the health history of relatives. The wizard may obtain vital statistics such as the sex and age of the patient, the weight of the patient, and if possible such doings as the blood pressure and cholesterol level of the patient. Next, the wizard will inquire as to the cost that the patient is willing to incur to obtain individual health care records. Finally, the wizard will ask a series of questions related to the detail preferences of the patient. In other words, these questions would be designed to obtain an accurate indication of what level of detail the patient truly needs or wants.

After the profile wizard has obtained the information described above, it automatically selects one of a number of predetermined profiles that can be used for this particular patient. Alternatively, the profiler can use the information provided by the patient to execute a routine that will generate a profile for the patient that is substantially unique.

As another option, the user will be allowed to select one of a number of standard profiles. The standard profiles are identified by a typical age and health condition of a patient who would use this particular profile, description of the profile itself. For example, one profile might be named "Male under 30 years of age, average weight, excellent health", and the profile description would be: "Minimum information obtained for ordinary office visits and minor surgeries not involving life threatening diseases". Another profile name may be "Female between 40 and 50 years of age, 40 pounds overweight, diagnosed with diabetes," and the profile description would be "Maximum information obtained for all medical care, excluding items costing less than $50 and excluding routine X-rays showing no significant disease."

Once the profile has been created or selected, the profile is used to selectively request information from health care Providers 21-23. For example, assume that a request-for-payment is received by My Record Application 16 from an insurance company. This request-for-payment indicates that Dr. Smith is requesting payment for gallbladder surgery and Dr. Black is requesting payment for anesthesiologist services.

My Record Application 16 would then check the profile of the patient and, for example, would determine that this patient wishes to obtain all the information possible about surgery, including photographs, and wishes to obtain all anesthesiology information including the identity of all drugs provided to the patient during surgery. In such case, My Record Application 16 would generate an appropriate request to doctors Smith and Black requesting the information.

In this example, assume that the patient has previously provided the electronic contact information for Dr. Smith, but only the address is known for Dr. Black. In such case, My Record Application 16 would generate an electronic data request that is sent directly to Dr. Smith, and Dr. Smith's computer or computer service would automatically generate a digital reply to this request. As previously noted, during the setup procedure, My Record Application 16 would have provided to the doctors an authorization from the patient to automatically provide digital data to My Record Application 16. Dr. Smith is highly sophisticated in terms of medical records in a digital format and all of his patient records are in a digital format and are available to the patient in accordance with applicable law.

In contrast, Dr. Black has no medical records in a digital format. All of his records are kept on paper. In addition, he does not have a fax machine or e-mail. Thus, there are two options remaining. The records may be requested by a voice request over the telephone or by a letter sent to Dr. Smith by regular mail. Again, the technique for requesting the information may have been predetermined during the initial setup by the patient. However, in the case of an anesthesiologist, it is likely that no such patient set up has been accomplished. In such case, My Record Application 16 will generate a letter that is electronically signed by the patient in a manner approved by law in the particular jurisdiction of the doctor, and the authorization letter would be sent directly to the doctor requesting the information. At the same time, the letter may request the doctor to automatically provide the information in the future, preferably, to My Record Application 16.

If a particular doctor has expressed a preference for voice communication by telephone, My Record Application 16 will generate request in a voice format and the computer will call the doctor and request information by voice. The computer voice will also request that the recipient of the telephone call verify that the recipient is a representative of a particular doctor and to verify receipt of the particular request. This may be done by requesting the recipient of the telephone call to say a particular word, and My Record Application 16 is provided with voice recognition equipment and software to determine whether the word was stated. Also, My Record Application 16 will record the spoken word to provide proof that the request was actually delivered.

Part of the information available to My Record Application 16 from a payer entity 20 could be voice information. For example, before a surgery it is common for insurance companies or other payer entities 20 to require the doctor, or the doctor's representative, to call the insurance company and have the surgery approved in advance. In such case, the insurance company often records the telephone call during which the authorization is requested. This authorization request is preferably sent by the insurance company automatically to My Record Application 16. Upon receiving the voice recording, My Record Application 16 performs a recognition routine in which it attempts to determine what was said during the conversation. The computer is programmed to be biased toward hearing words that are commonly used in the medical or health care community. For example, the computer is programmed to hear words related to surgery. For example, the routine will be biased to hear the word "surgery" or any word that might indicate surgery, such as "appendectomy" or "hysterectomy". In fact, almost any word ending with the "Tomy" sound will be interpreted to be some type of surgery. It may be biased to "hear" and interpret acronyms like "OR" meaning "operating room" or "PRN" meaning "as needed". Once the computer recognizes a particular word or phrase, it will re-evaluate words in the near vicinity with a bias toward interpreting nearby words consistently. For example, if "OR" is recognized, then another nearby phrase like "happen deck tommy" will be re-evaluated and will be interpreted as "appendectomy".

If the computer recognizes, or thinks it recognizes, a word indicating surgery, it may be programmed to conduct a further analysis of the patient records to determine whether any reports or alerts are necessary. For example, it will check the patient's health history questionnaire to determine whether the patient has indicated any allergic reactions to drugs that might be used during surgery. Likewise, it will check the patient's health history to determine whether the patient is taking any drugs that might interact with a drug that is typically used during surgery. If any drug allergies or drug interactions are discovered, My Record Application 16 will send the patient an e-mail, fax or phone call and will send the doctor an e-mail, fax and/or phone call which includes a report of information that may be of interest. Depending on preferences defined in the patient's profile, My Profile 18, the report may be characterized as an alert or merely a for-your-information report. In this way, both the patient and the doctor will be given information that may be relevant and may indicate possible risks.

When medical information is received from any source, it may be in a variety of formats. Most preferably it will be in a standard electronic form, such as XML file, or in some other format in which fields of information are identified by the order of the information and symbols that separate the fields. For example, a preferred format would include a comma separating every filed of information in a text file with the first word in every field identifying the type of information. This is commonly known as a comma-delimited ASCII text file. Information from any database can be translated into this standard format and thus the standard format enables easy transfer of data from any database.

In the case of medical information that is not available in a database format, or is not available in the standardized format, it will need to be recognized and translated. For example if paper records are provided, the records are converted to electronic image files and then various optical character recognition (OCR) programs are use to automatically translate the typed test and the handwritten text to electronic text, and the text is searched for information that may be introduced into a database supporting My Record Application 16. The computer at My Record Application 16 is programmed with a search engine, to look for a large number of words that are likely to appear in medical records. One such word would be "cholesterol" and abbreviations of "cholesterol". When the word is found, the program searches for nearby expected words, such as "ldl", "hdl", "total" and the like. In addition to searching the text file for the expected words, the original image file is examined again to look for the expected words. In this second examination the program is biased to find the expected words. For example if the word "bdl" is found, it will be interpreted as "hdl".

As used herein, expected words would include expected numbers. When "cholesterol" is found expected words would be two and three digit numbers less than 400. So, if "797" is found on the same line as "total" and cholesterol, it would be interpreted as "197" or "297" or "397", depending on what the first digit most resembled and what else is found. For example, if the number "229" is found on the same line as "ldl", the number "797" will be interpreted as "297" because the "ldl" number is normally less than the total, but within 100 points of the total. The number "297" is therefore entered in the database as the total cholesterol and "229" is entered as the ldl cholesterol number. The database will be relatively simple in structure, having fields to identify the patient, dates, doctors, the type of medical information and the medical information itself. The medical information may be contained in multiple fields, some of which will be number fields and others being text and graphics fields. The user may define specific types of data that it would like to chart. Records received will be translated using character recognition and the data extracted or e-mails sent to user indicating data is probably available but may require manual interpretation and extraction.

A database supporting My Record Application 16 typically uses designated analysis parameters and alarm limits from designated analysis parameter and alarm limit sets to assist with things like tabular and graphical trend reporting.

All medical records are translated in a manner similar to that described above using a combination of optical character recognition and logic based on the identification of the type of medical record under consideration and the expected content of particular types of medical records. The database will also record a confidence level with all translated information and will map the information to the original image so that the user can check the information against the image. For example, if the database displayed a number "197" as the total cholesterol, but it was marked with red question marks, that would indicate a low confidence level, and the user could click on the number to see the original image, which would show an image of "297" as the total cholesterol.

The difficulty and inherent uncertainty of translating optical images of documents illustrates why standardized file formats should be used to transfer data whenever possible. Any known file format is preferable to an image file because generally any digital data file format can be translated to another format with an accuracy approaching 100%.

A software tool is also provided that searches the database for repetitive events and accumulates the repetitive events into a single location and optionally reformats the data. The user may define in his profile events or data that he wishes to accumulate for obtaining frequency of occurrence data, usually charts and graphs of the data. For example, the profile may be set to accumulate cholesterol information, and the tool may search for cholesterol values and assemble all data related to cholesterol into a single location. Then, optionally, it can reformat the data, such as placing the data in a chart or creating a graph showing the cholesterol values as they change over time. This tool may be set to look for a particular type of repetitive data, such as a particular parameter (eg. blood pressure, white blood cell count, etc) or it may be set to search for any type of repetitive data and give the user an opportunity to accept or decline a report on any repetitive data located by the search. When the tool is directed to search for particular types of data it is presumed important and it will be found and displayed first, preferably in an order of importance set by the user. Any additional data found by the tool may be reported last and the user may be given the choice of seeing the additional reports on the additional data, or temporarily refusing such reports, or permanently setting the tool to never report a particular type of data.

The database and file formats used in My Record Application 16 will incorporate codes and standardized vocabulary used in the health care field including Medicare coding, CPD (common procedural terminology), ICD-9 (International classification of Diseases), and Standardized vocabulary such as developed by Health Level Seven (HL7)(see www.HL7.org) and the American Standards Committee X12 (X12)(see www.X12.org).

My Record Application 16 is also programmed to perform automatic analysis of medical data, but the automatic analysis may be turned off when the patient creates his My Profile 18. Thus, for example, a patient could choose in his My Profile 18 for My Record Application 16 to not inform the patient or the doctor about possible adverse drug interactions between a drug taken by the patient and a drug typically used during surgery. In addition to the various automatic analysis of information that may be performed by the computer, there are numerous manual types of analysis that may be performed by My Record Application 16 in response to a manual request by the user. For example, the user may choose an option allowing the user to perform various different types of analysis on the data in a website. In this example, a particular user may wish to obtain a graph of the red blood cell count in his blood over last two years. By clicking on this option in the analysis section of the program, the user instructs My Record Application 16 to search the patient's records for all information concerning red blood cell counts. The computer will then provide the information in a human readable form and will interpret the information to the extent possible and generate a graph indicating trends. If records are in doubt, the patient may be asked to verify the accuracy of the data. For example, if a red blood count was determined from a scanned image, the image may be shown to the user with a request to verify that the blood count was accurately determined by the computer. In one embodiment, all information collected by My Record Application 16 will be displayed to the user in its rawest form and the user is requested to verify the accuracy of the information. For example, if My Record Application 16 found a graphics file, recognized the graphics as text, and converted it to electronic text (such as ASCII), My Record Application 16 displays the graphical form of the data (an image) and the electronic form of the data (text) and requests the user to verify accuracy. Also, the user is given the option of correcting the electronic data (e.g. text).

In addition to receiving request-for-payment from a payer entity 20, such as an insurance company, the patient may request the Providers 21-23 to transmit a request-for-payment directly to the insurance company and simultaneously to My Record Application 16. If the provider is doing this, the user may choose not to request the same information from the insurance company. On the other hand, receiving duplicate information and comparing the duplicate information will provide a measure of safety by double checking information provided by the insurance company or other third-party payer. Thus, most patients will chose to receive the request-for-payment information from both sources.

One of the features of My Record Application 16 is an information log listing all pertinent received information and any additional information and at least the original site of the received information, including additional information that may not have been requested. The log lists all pertinent information requested, its method for delivery, the party to whom the request was made, and the identity of the information requested. The patient can view the status of all information requests or just those pending completion. If no response has been received from the healthcare provider after an appropriate waiting period, successive follow-up attempts to acquire the requested data will be initiated by the system. When the number of retries specified is exhausted or a refusal to transmit the data is received from the healthcare provider, the patient is informed of the unsuccessful request sequence, identifying the health care provider, and querying the patient in some way such as to acknowledge or to specify further follow-up actions.

Another of the features of My Record Application 16 relates to the fact that it is owned and controlled by the patient. Thus, the web site includes a feature whereby a user can connect to the web site and synchronize a home computer with the information provided at My Record Application 16. Synchronization means that any data found in My Record Application 16 that is not found on My Computer 14 is transferred to My Computer 14, and vice versa. Thus, if a user provides additional information about his health or health history on his own personal computer without connecting to the Internet, such information will be provided to My Record Application 16 upon the next synchronization. Typically, My Record Application 16 will be configured to offer automatic synchronization each time it detects a discrepancy between the information on My Computer 14 and the information on My Record Application 16.

Typically the new information found on My Computer 14 will be transferred to My Record Application 16, and new information on My Record Application 16 will be transferred to My Computer 14. However, if a particular piece of information has been changed at both places, then the both My Computer 14 and My Record Application 16 will record all of the information from both locations and will send an alert the patient regarding the discrepancy. Conflicting records may also be flagged in both My Computer 14 and My Record Application 16. These flagged records may then be brought to the attention of the user and the user will be requested to delete one of the records.

One of the advantages of using the request-for-payment information is the consistency of the information. In most cases, the majority and perhaps the only information on the request-for-payment will be codes specified by ANSI 837. These codes are identified at www.DISA.org. My Record Application 16 is programmed to recognize the codes, interpret the codes into a human readable format, and correlate the codes to My Profile 18. For example, suppose a code is found indicating an appendectomy. This code would be correlated to the surgical profile of the patient, My Profile 18. If the surgical profile indicates that the patient wants information from the doctor about surgery, but wants a minimum of the information, My Record Application 16 will communicate a request to the doctor requesting specific types of information about the surgery and excluding other types of information. For example, in the case of an appendectomy, the user may request the physician's notes and observations about the surgery, but request no imaging information such as photographs that may have been taken during surgery. Likewise, the patient may exclude any requests for information as to the type and amounts of drugs used by the anesthesiologist.

One of the features of the present system is that it allows information from Providers 21-23, such as doctor information, to be integrated into one the database with information provided by the patient. For example, the patient may periodically enter information concerning his health such as weight, the number of pushups done each day, blood pressure, calorie intake, the date and length of seizures, episodes of vomiting, and the like. This information will be recorded in the log in the same manner, or a similar manner, to the information provided by health care Providers 21-23. The database will identify the particular person providing each item of the information. For example, if a doctor provides information, a field in the data base will identify that doctor. If a patient provides information, a field in the data base will identify the patient or other individual or organization that provided information.

With this format of information, a user can more efficiently analyze the combination of his self provided information and Provider 21-23 information. Likewise, the combined information of the patient and the Providers 21-23 would be useful to the Providers 21-23. For example, a Provider 21 may notice that the blood pressure measured at his office is consistently higher than the blood pressure measured by the patient at home. This could indicate faulty equipment at one place or another, or it could indicate that the patient has higher blood pressure at the doctor's office due to anxiety and fear. Likewise, in the case of a patient having seizures, the health care Provider 21 would probably find it useful to have patient provided information concerning the timing and duration of seizures. Such information would be particularly useful to the health care Provider 21 who is attempting to control the seizures in an emergency situation. Thus, the provision of integrated patient records and health provider records into a single combined log and a single combined data base is an important feature of the invention.

A search engine is also provided by My Record Application 16. The search engine allows the patient to search for specific terms internally within the patient's own records on the My Record Application 16. Thus, a patient can efficiently assemble all information related to a particular disease or condition by searching on a key word or combinations of key words. For example, the patient may perform a search specifying "Seizure minutes". In such case, any patient record that included both words would be found and listed, which would enable the patient to quickly ascertain the duration of seizures in minutes over a number of days. Also, the user would be provided with search engine capabilities enabling a user to search the Web for particular terms.

The database and log maintained on My Record Application 16 are also organized into families. That is, each log is identified as to the patient and the family to which the patient belongs. Thus all of the logs of a particular family can be simultaneously identified, and printed. Likewise, the data base includes a field that identifies the particular family and family member to which this particular record relates. This feature allows the patient to search all of the family records for a particular matter of concern. For example, a patient may wish to identify all of the seizures that have occurred in a particular family. By assembling those records collectively, a pattern may emerge that helps explain the seizures. For example, an environmental feature may be discovered that is triggering the seizures.

As described above, it is preferable that the Providers 21-23 and third-party payers (such as insurance companies) be requested to automatically provide certain types of the information. However, not all Providers 21-23 and third-party payers will be 100 percent reliable. Therefore, a reminder feature is provided in My Record Application 16 whereby known third-party payer entities 20 and known Providers 21-23 for a particular patient are periodically requested to provide information. Typically, a payer entity 20 that did not report anything for over three months would be automatically queried as to whether they had provided the requested information during the previous three months. In the case of a particular doctor, the program may be set to never query the doctor or query the doctor at regular but longer intervals. For example, if nothing had been received from the doctor for six months, a query is the generated and sent to the doctor through a preferred communications mode ranging from a digital electronic request to paper mail. This reminder feature is considered to be a backup feature of the invention, but the system could be organized around the reminder feature so that the doctors are always requested to provide information and they are not required to automatically send the information. Some third-party Providers 21-23, such as non-computerized doctors, would have difficulty remembering to provide information automatically, and therefore, it may be preferable in some instances to use a system that queries the insurance companies for information.

Figure 2:
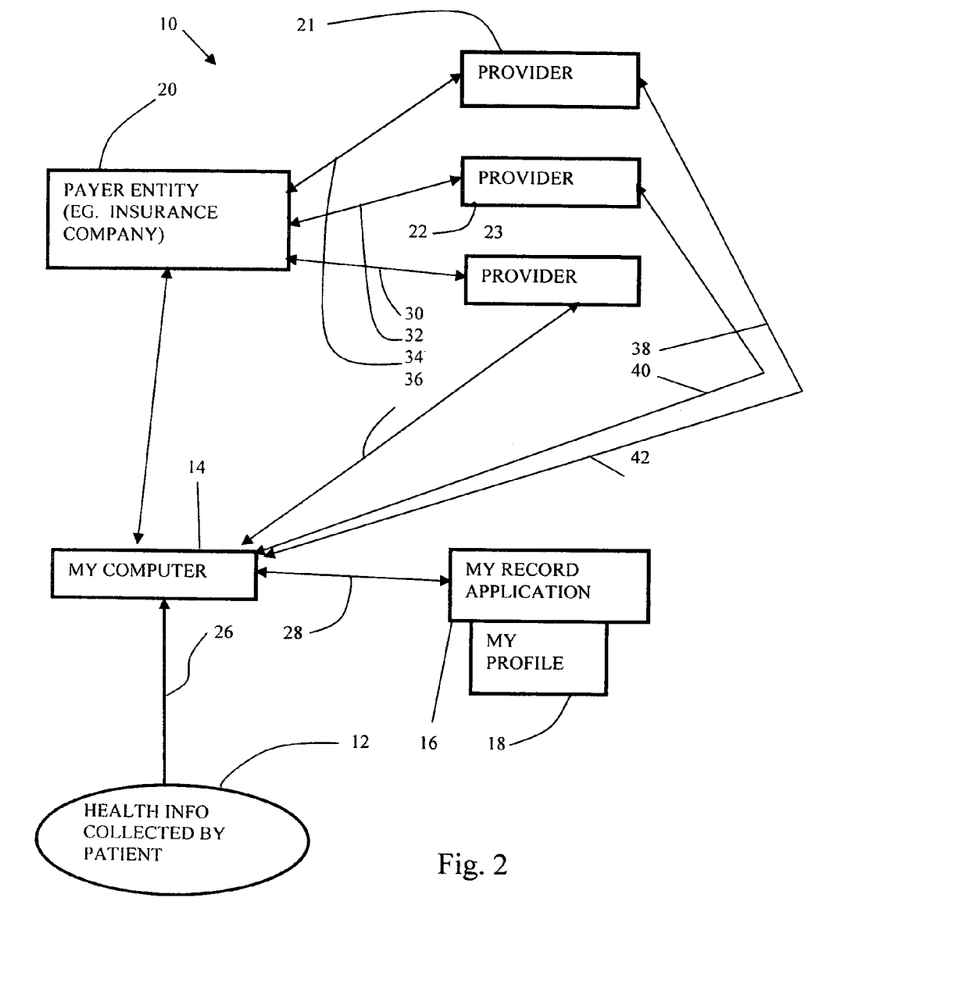
FIG. 2 is block diagram illustrating a personal computer communicating with a patient's computer, a third party payer entity 20, and health care providers 21, 22 and 23.

While it is preferred to provide this information on a website for numerous patients, it should be understood that the function of My Record Application 16 could be performed on a patient's individual computer, and it is not absolutely necessary that the information be maintained in a web-based application. It is convenient to use web browsers to obtain and manipulate data and that same convenience may be utilized even if a patient's computer is directly running the computer program only for the patient. However, if desired, the patient's computer program can be customized so that browsers are not used and, a more direct input system is provided. For example, a simple menu selection system may be provided.

In one embodiment, the log produced by My Record Application 16 is not only complete but it includes analysis of events, non-events and reminders. All activities or events, including non-events, are recorded in the log. When any information is received, the information is stored and the storage location of the information is recorded in the log along with additional information such as the date of the receipt and a description of the information. The description is automatically generated by selecting key words from the received information, and My Record Application 16 may be set to request confirmation of the description, or to not request confirmation, as desired.

In addition, My Record Application 16 also records non-events in the log. For example, if My Record Application 16 identifies information that may exist, but the program does not request the additional information based on the preferences set in My Profile 18, the log generated by My Record Application 16 includes both the identity of the information that was actually requested and the identity of information that was not requested. As another example of recording non-events, if additional information is requested but is not received after a set period of time, My Record Application 16 logs the non-receipt of the information and it generates a reminder to the user of such non-receipt.

Received information is automatically compared to the log of requested information and My Record Application 16 automatically determines whether the received information corresponds to requested information. If there is a correspondence, My Record Application 16 updates the log to indicate that the requested information was received. Again, My Record Application 16 may be set to request confirmation of the automatic determination. That is, when My Record Application 16 automatically determines that certain information is received, the user may be requested to confirm that the received information actually corresponds to the requested information. However, as before, this confirmation feature may be turned off and the automatic determination is accepted.

Having described a preferred embodiment to illustrate the present invention, it will be understood that the described embodiment is not intended to limit the scope of the invention, which is capable of numerous rearrangements, modifications and substitutions of parts, without departing from the scope of the invention as defined by the appended claims.

What is claimed is:

1. A method for updating a patient-controlled and patient-centered electronic personal medical record database comprising:
   providing a database of medical records for one or more patients including a patient identifier, a patient profile indicating the type of medical records desired by the patient, and information relating to the healthcare of the one or more patients;
   using a computer and computer software to request and receive the patient's explanation-of-benefits information from a third party payer using the computer software to identify and interpret the received explanation-of-benefits information to produce an interpretation;
   using the interpretation to selectively generate a trigger for requesting medical records from a healthcare entity, the trigger being generated if a medical record is suggested to exist by the interpretation step and if the patient profile in the database indicates that the medical record is the type of medical record desired by the patient;
   requesting the identified medical record when the trigger is generated;
   receiving the identified medical record; and
   updating the database using at least a portion of the received medical record.

2. The method of claim 1 further comprising providing the database with a plurality of data fields and using the software to translate and extract data from at least a portion of the medical record and parse the data into data fields.

3. The method of claim 2 wherein the translating uses a standardized vocabulary.

4. The method of claim 1 further comprising anticipating and reporting possible need for future health care actions based on receiving explanation-of-benefits information.

5. The method of claim 1 further comprising logging activities performed by the method to produce:
   an information log listing the received explanation-of-benefits information and received medical records and at least the computer location of the received explanation-of-benefits information and received medical records;
   a request log listing information requested by the method including the party to whom the request was made and the identity of the information requested; a tickler identifying additional information that was requested and indicating whether each item of the additional information was or was not received.

6. A method for updating a patient-controlled and patient-centered electronic personal medical record database comprising:
   providing a database of medical records for one or more patients including a patient identifier, a patient profile indicating the type of medical records desired by the patient, and information relating to the healthcare of the one or more patients;
   using a computer for receiving and automatically interpreting the patient's explanation-of-benefits information or request-for-payment information to produce an interpretation;
   using the interpretation to selectively generate a trigger for requesting medical records from a healthcare entity, the trigger being generated if a medical record is suggested to exist by the interpretation step and if the patient profile in the database indicated that the medical record is the type of medical record desired by the patient as defined in the patient's profile;
   requesting the identified medical record when the trigger is generated;

receiving the identified medical record;

updating the database using at least a portion of the received medical record.

7. The method of claim 6 further comprising:

logging the requests for medical records to produce an information log listing requests for medical records that were produced;

identifying information that was requested but not received;

making additional attempts to obtain information that was requested but not received; and informing the patient of unsuccessful requests for information; and identifying the health care provider who did not provide information after being requested to do so.

8. A method for automatically creating and managing personal medical records comprising:

identifying in a patient profile types of the patient's medical record information that the patient wants to obtain and save wherein the identified types comprise a selected subset from the larger set of the patient's medical record information;

receiving one or more of:

(a) explanation-of-benefits information regarding a patient, and (b) request-for-payment information regarding the patient's health care;

computer processing the one or more of the received explanation-of-benefits information and request-for-payment information to interpret data contained thereon and produce an interpretation that suggests the existence of types of medicals records;

comparing the interpretation with the patient profile to determine a medical record of the type the patient wants to obtain and save and of a type that was suggested to exist by the interpretation;

using results of the comparison to selectively generate a trigger;

using the trigger to automatically request an identified medical record that is a type that the patient wants to obtain and save.

\* \* \* \* \*